United States Patent
Fukushima

(10) Patent No.: US 10,842,355 B2
(45) Date of Patent: *Nov. 24, 2020

(54) ENDOSCOPE APPARATUS

(71) Applicant: FUJIFILM Corporation, Tokyo (JP)

(72) Inventor: Kimitake Fukushima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 228 days.

This patent is subject to a terminal disclaimer.

(21) Appl. No.: 15/960,566

(22) Filed: Apr. 24, 2018

(65) Prior Publication Data

US 2018/0235446 A1    Aug. 23, 2018

Related U.S. Application Data

(63) Continuation of application No. 15/062,174, filed on Mar. 6, 2016, now Pat. No. 10,136,797.

(30) Foreign Application Priority Data

Mar. 31, 2015    (JP) ................................. 2015-072636

(51) Int. Cl.
    *A61B 1/00*    (2006.01)
    *A61B 1/012*    (2006.01)

(52) U.S. Cl.
    CPC ...... *A61B 1/00126* (2013.01); *A61B 1/00114* (2013.01); *A61B 1/00117* (2013.01); *A61B 1/00013* (2013.01); *A61B 1/00163* (2013.01); *A61B 1/012* (2013.01)

(58) Field of Classification Search
    CPC . A61B 1/012; A61B 1/00013; A61B 1/00126; A61B 1/00114; A61B 1/00117; A61B 1/00163
    See application file for complete search history.

(56) References Cited

U.S. PATENT DOCUMENTS

| | | | | |
|---|---|---|---|---|
| 3,726,272 A * | 4/1973 | Fukami | .............. | A61B 1/00165 600/126 |
| 4,416,268 A * | 11/1983 | Hagino | .............. | A61B 1/00119 600/132 |
| 4,589,404 A * | 5/1986 | Barath | .................... | A61B 1/042 348/359 |
| 6,374,025 B1 * | 4/2002 | Iriyama | .................... | G02B 6/32 385/116 |

(Continued)

*Primary Examiner* — Timothy J Neal
*Assistant Examiner* — William B Chou
(74) *Attorney, Agent, or Firm* — JCIPRNET

(57) ABSTRACT

Provided is an endoscope apparatus that can improve the airtightness of a space within a connector part where an optical semiconductor element or the like is present. The endoscope apparatus includes a connector part that is connected to an external device and transmits and receives light signals to and from the external device. The connector part includes a hollow metal member having two openings that communicate with each other, a light emitting element that is press-fitted and fixed to one opening side of the hollow metal member so as to be capable of sealing the periphery of the one opening, a lens that is provided on the other opening side of the hollow metal member, a fixing member that fixes the lens to the hollow metal member, and an O ring that is pressed by the fixing member and seals a gap between the lens and the hollow metal member.

20 Claims, 5 Drawing Sheets

(56) References Cited

U.S. PATENT DOCUMENTS

| | | | | |
|---|---|---|---|---|
| 6,969,348 | B2* | 11/2005 | Araii | A61B 1/00163 362/574 |
| 10,136,797 | B2* | 11/2018 | Fukushima | A61B 1/00114 |
| 2006/0116550 | A1* | 6/2006 | Noguchi | A61B 1/015 600/132 |
| 2006/0173242 | A1* | 8/2006 | Navok | A61B 1/00066 600/133 |
| 2007/0162095 | A1* | 7/2007 | Kimmel | A61B 1/00105 600/109 |
| 2010/0172615 | A1* | 7/2010 | Ben Bakir | B82Y 20/00 385/49 |

\* cited by examiner

ENDOSCOPE APPARATUS

CROSS-REFERENCE TO RELATED APPLICATIONS

The present application is a continuation application based on U.S. patent application Ser. No. 15/062,174 and claims priority under 35 U.S.C. § 119 to Japanese Patent Application No. 2015-072636, filed on Mar. 31, 2015. The above application(s) is hereby expressly incorporated by reference, in its entirety, into the present application.

BACKGROUND OF THE INVENTION

1. Field of the Invention

The present invention relates to an endoscope apparatus.

2. Description of the Related Art

Electronic endoscope systems guide the light from a light source device to an electronic endoscope that is a scope, radiate this light from a distal end part to a region to be observed, and pick up an image of the region to be observed, using a charge coupled device (CCD) disposed at the distal end part. In this type of electronic endoscope system, the electronic endoscope is detachably connected to an external device, such as the light source device or a processor device, by a connector part via a cable, and video signals are supplied to a monitor via the processor device.

In a case where the above-described electronic endoscope systems are used particularly for medical diagnosis, the cleaning work of cleaning and disinfecting the electronic endoscope inserted into a body cavity of a subject is required. For this reason, when performing the cleaning work, separate airtight means, such as a waterproofing cap, can be mounted on an electrical connector part of the electronic endoscope that is an electrical contact point for performing communication with the external device. However, since this airtight means is relatively large and also has weight, time and effort are required for the attachment and detachment of the airtight means to the connector part. Additionally, if the cleaning work is performed without the mounting of the airtight means, the inside of the electronic endoscope may be submerged from the electrical connector part. In contrast, in a case where an optical connector part that is not electrically connected to the external device is provided in the electronic endoscope, the cleaning work of the electronic endoscope can be performed by adopting a waterproof structure for this optical connector part, without using the above-described airtight means (for example, JP1998-155740A (JP-H10-155740A) and JP2013-208187A).

Patent Literature 1: JP1998-155740A (JP-H10-155740A)
Patent Literature 2: JP2013-208187A

SUMMARY OF THE INVENTION

When the cleaning work is performed in a state where the above-described electronic endoscope is detached from the external device, a cleaning liquid or water may be applied to the optical connector part of the electronic endoscope with high pressure. For this reason, high airtightness is particularly required for a space within the optical connector part where an optical semiconductor element or the like is provided.

The invention has been made in view of the above-described circumstances, and an object thereof is to provide an endoscope apparatus that can improve the airtightness of a space within a connector part where an optical semiconductor element or the like is present.

An endoscope apparatus disclosed of one aspect of the invention comprises a connector part that is connected to an external device and transmits and receives a light signal to and from the external device. The connector part comprises a hollow metal member having two openings that communicate with each other; an optical semiconductor element that is fixed to one opening side of the hollow metal member so as to be capable of sealing the periphery of the one opening; a lens that is provided on the other opening side of the hollow metal member; and a first sealing member that fixes the lens to the hollow metal member and seals a gap between the lens and the hollow metal member.

According to the invention, it is possible to provide the endoscope apparatus that can improve the airtightness of the space within the connector part where the optical semiconductor element or the like is present.

DESCRIPTION OF THE PREFERRED EMBODIMENTS

Hereinafter, a preferred embodiment of the invention will be described with reference to the drawings.

Figure 1:
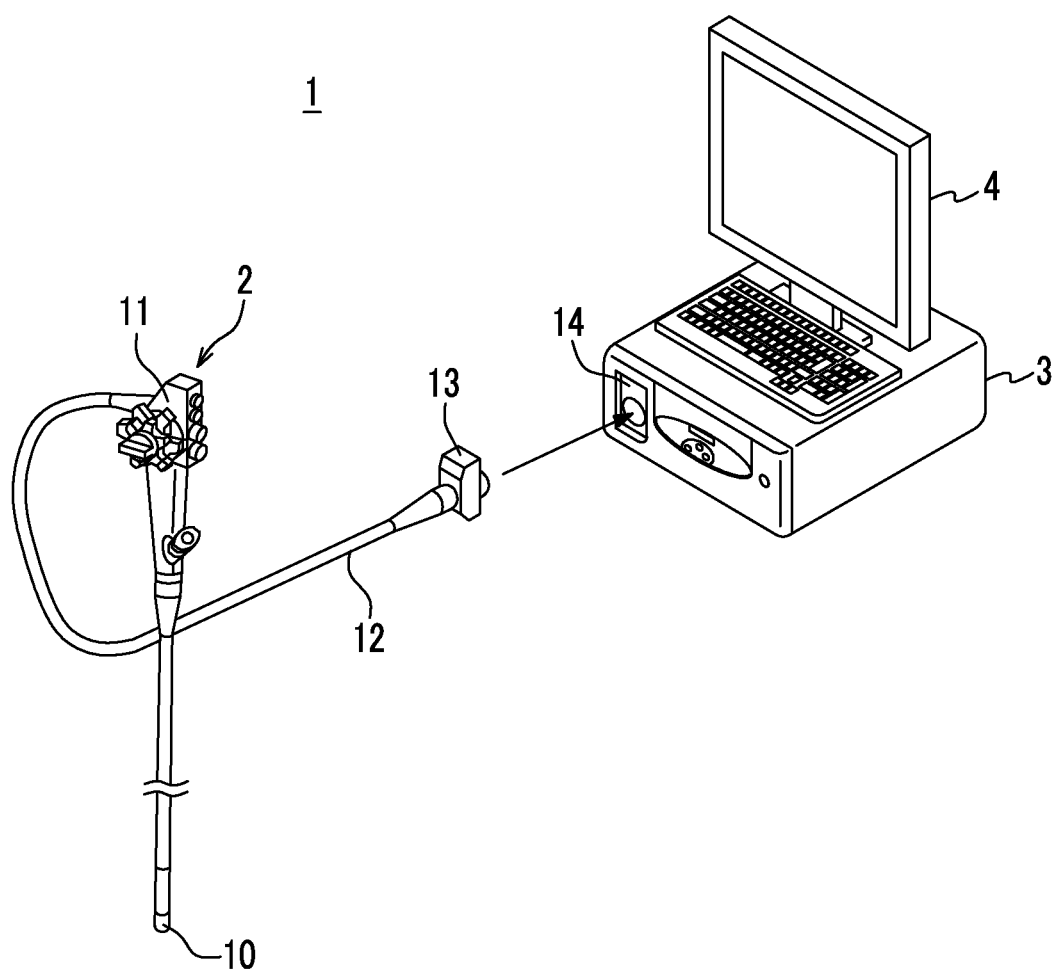
FIG. 1 is an appearance view of an example of an electronic endoscope apparatus for describing an embodiment of the invention.

FIG. 1 illustrates the configuration of an example of an electronic endoscope system for describing the embodiment of the invention.

An electronic endoscope system 1 includes an electronic endoscope 2 that is an endoscope apparatus, a processor device 3 that is an external device, and a monitor 4 that is connected to the processor device 3.

The electronic endoscope 2 has an insertion part 10 that is inserted into a body cavity of a subject, an operating part 11 that is connected to the insertion part 10, and a universal cord 12 that extends from the operating part 11. A connector 13 is provided at the terminal of the universal cord 12, the connector 13 is connected to a connector 14 provided in the processor device 3, and the electronic endoscope 2 and the processor device 3 are connected together via both the connectors 13 and 14. The electronic endoscope 2 connected to the processor device 3 via both the connectors 13 and 14 is capable of communicating with the processor device 3 by transmitting and receiving light signals.

Figure 2:
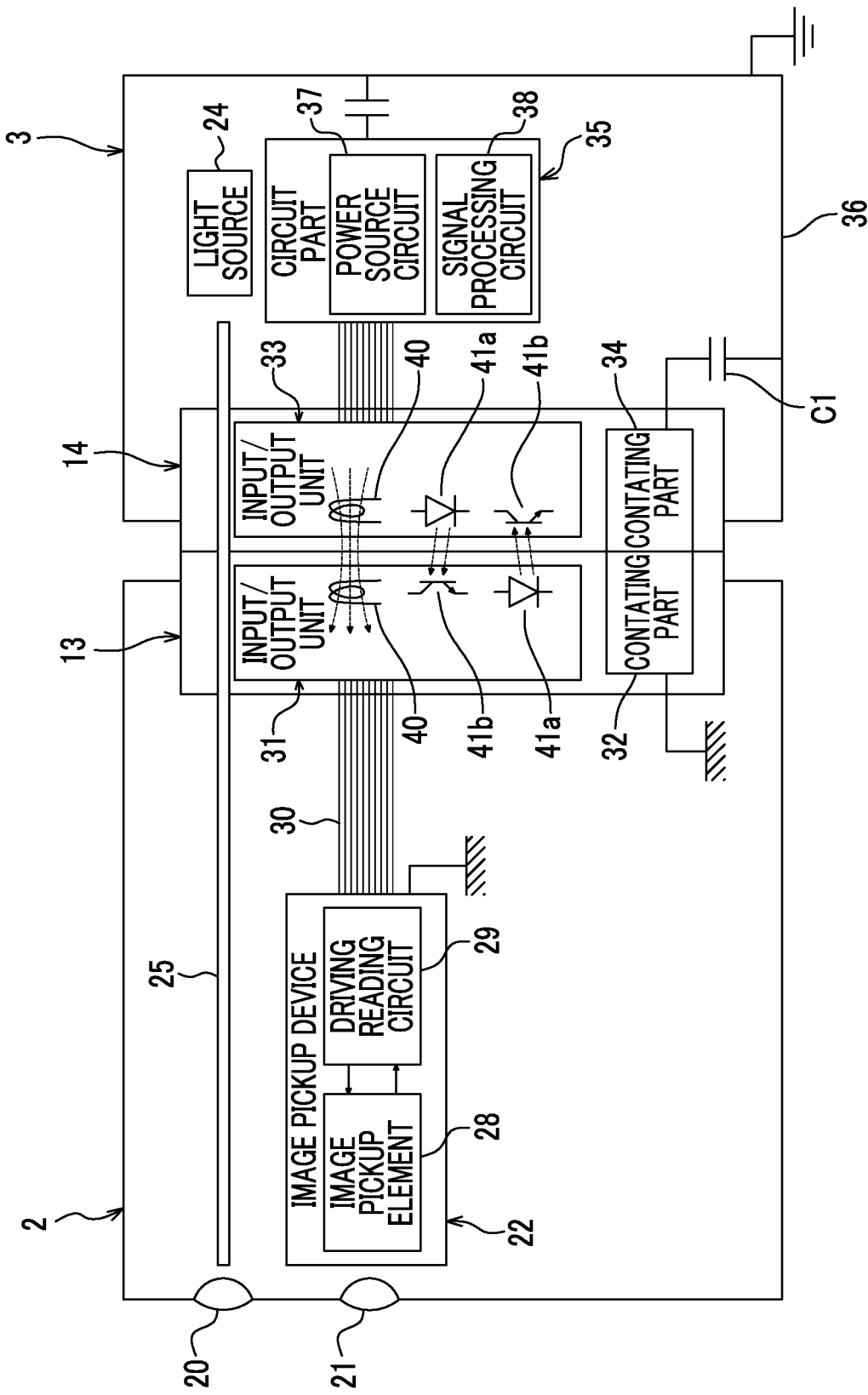
FIG. 2 is a functional block diagram of the electronic endoscope apparatus of FIG. 1.

FIG. 2 illustrates a functional block of the electronic endoscope system 1.

A distal end part of the insertion part 10 of the electronic endoscope 2 is provided with an illumination optical system 20 that radiates illumination light, an objective optical system 21, and an image pickup device 22 that receives an image focused by the objective optical system 21.

The illumination light radiated from the illumination optical system 20 is produced by a light source 24 provided in the processor device 3, and is guided from the light source 24 to the illumination optical system 20 by a light guide 25 encapsulated in the universal cord 12 (refer to FIG. 1).

The image pickup device 22 drives an image pickup element 28, such as a charge coupled device (CCD) image sensor or a complementary metal-oxide semiconductor (CMOS) image sensor, and a driving reading circuit 29 that drives the image pickup element 28 and reads image signals from the image pickup element 28. The driving reading circuit 29 is configured to include, for example, a driver for the image pickup element 28, an amplifier that amplifies the image signals read from the image pickup element 28, an A/D converter that converts the image signals into digital signals to output the converted digital signals, and the like.

The operating power of the image pickup element 28 and the driving reading circuit 29, a control signal input to the driving reading circuit 29, and the image signals output from the driving reading circuit 29 are transmitted to a wiring group 30 encapsulated in the universal cord 12, and are transmitted and received between the electronic endoscope 2 and the processor device 3 via the connectors 13 and 14.

The connector 13 is provided with an input/output unit 31 that transmits and receives the electric power and the signals to and from the connectors 14 of the processor device 3, and a contacting part 32 that is connected to the ground of the electronic endoscope 2.

The processor device 3 has an input/output unit 33, a contacting part 34, and a circuit part 35.

The input/output unit 33 is provided in the connector 14, and transmits and receives the electric power and the signals to and from the connector 13 of the electronic endoscope 2 connected to the connector 14. Additionally, the contacting part 34 is also provided in the connector 14, and is connected to a housing (ground) 36 of the grounded processor device 3 via a capacitor C1.

The circuit part 35 has, for example, a power circuit 37 that produces electric power to be supplied to the image pickup element 28 and the driving reading circuit 29 from a commercial power source (not illustrated), and a signal processing circuit 38 that processes signals of the driving reading circuit 29. The signal processing circuit 38 is configured to include, for example, a control circuit that controls the operation of the driving reading circuit 29, an image processing circuit that performs various signal processing, such as white balance correction, on image signals, and produces image data, and the like. Image data produced by the signal processing circuit 38 is displayed on the monitor 4 (refer to FIG. 1).

The input/output unit 31 of the connector 13 and the input/output unit 33 of the connector 14 are insulated from each other, and transmit and receive the electric power and the signals. In addition, in the present specification, the "insulation" means that conductors for transmitting electric power and signals are separated from each other, and the conductors are separated from each other between the input/output units 31 and 33.

In an illustrated example, coils 40 are respectively provided in the input/output units 31 and 33, and the pair of the coils 40 are arranged to face each other with non-contact in a state where the connectors 13 and 14 are connected to each other, and transmit electric power with mutual insulation being maintained using electromagnetic induction.

Additionally, in each of the input/output units 31 and 33, a light emitting element 41a that is an optical semiconductor element is provided on an output side for each signal, and a light receiving element 41b that is an optical semiconductor element is provided on an input side, and the pair of the light emitting element 41a and the light receiving element 41b are arranged to face each other with non-contact in a state where the connectors 13 and 14 are connected to each other, and transmit electric power with mutual insulation being maintained using light.

In addition, the electric power with insulation being maintained is not limited to the above method. For example, a magnetic resonance system that uses the coils 40 as resonators can also be used for the transmittance and reception of the electric power.

Meanwhile, the contacting part 32 of the connector 13 and the contacting part 34 of the connector 14 come into contact with each other in a state where the connectors 13 and 14 are connected to each other, and the ground of the electronic endoscope 2 and the housing 36 of the processor device 3 are electrically connected to each other.

In addition, in the above-described electronic endoscope system 1, the image pickup device 22 (the image pickup element 28 and the driving reading circuit 29) has been illustrated as an electronic device mounted on the electronic endoscope 2. However, the electronic device mounted on the electronic endoscope 2 is not limited to the image pickup device 22. For example, a configuration in which the illumination light produced by the light source 24 of the processor device 3 is guided to the distal end part of the insertion part 10 of the electronic endoscope 2 by the light guide 25 and is radiated from the illumination optical system 20 is provided in the above-described electronic endoscope system 1. However, it is also possible to provide the distal end part of the insertion part 10 with a light emitting diode (LED) and its drive circuit and to produce illumination light by the LED.

Figure 3:
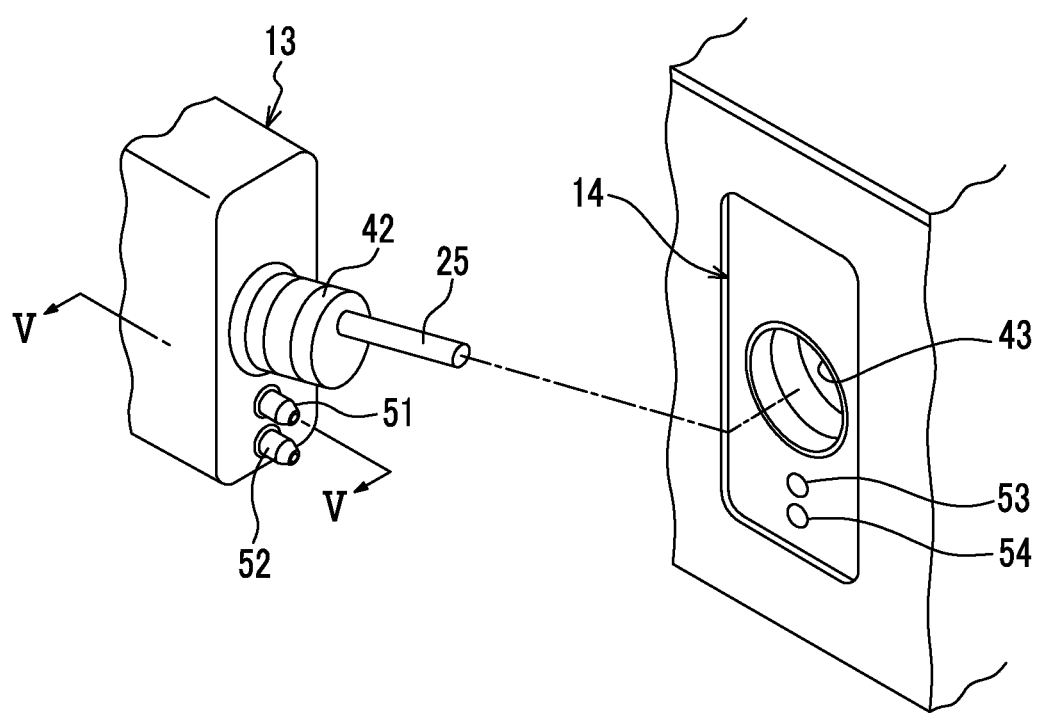
FIG. 3 is a view illustrating the configuration of respective connectors of an electronic endoscope and a processor device of FIG. 1.
Figure 4:
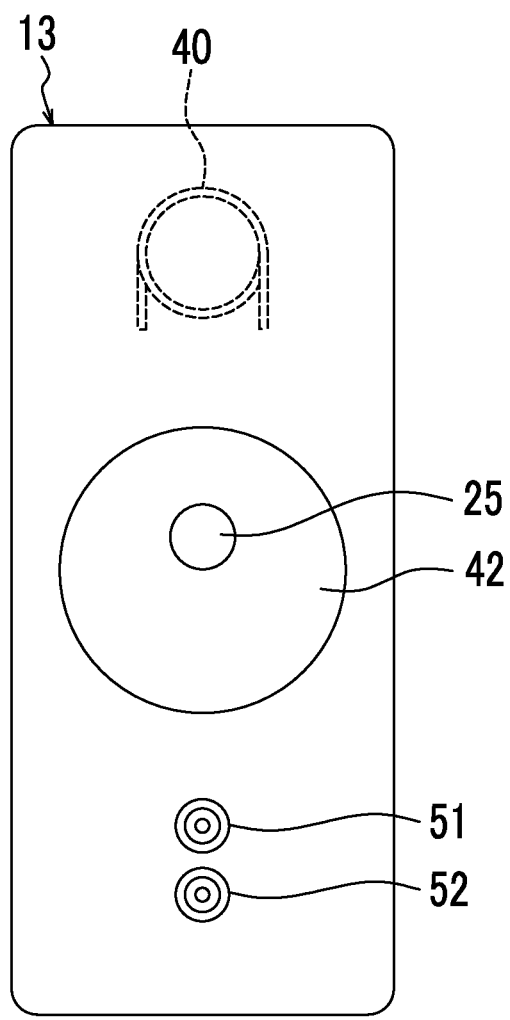
FIG. 4 is a front view of the connector of the electronic endoscope of FIG. 3.

FIGS. 3 and 4 illustrate the configuration of the connector 13 of the electronic endoscope 2 and the connector 14 of the processor device 3.

The connector 13 of the electronic endoscope 2 has a fitting part 42 that is formed in a convex shape, and the connector 14 of the processor device 3 has a fitting part 43 that is formed in a concave shape. The fitting parts 42 and 43 are fitted to each other with the mutual connection between the connectors 13 and 14, and the fitting part 42 of the connector 13 is covered with the fitting part 43 of the connector 14.

In the illustrated example, the convex fitting part 42 is provided at a substantially central part of the connector 13, and a terminal part of the light guide 25 that guides illumination light is held by the fitting part 42. Additionally, one side part of both side parts of the connector 13 that sandwiches the fitting part 42 therebetween is provided on the coil 40 that transmits and receives electric power, and the other side part is provided with a light emitting connector part 51 and a light receiving connector part 52 that are connector parts formed in a convex shape and that transmit and receive signals. Additionally, the connector 14 is provided with two fitting parts 53 and 54 that are formed in a concave shape separately from the fitting part 43. The light emitting connector part 51 is fitted to the fitting part 53 with the mutual connection between the connectors 13 and 14, and the light receiving connector part 52 is fitted to the fitting part 54 with the mutual connection between the connectors 13 and 14.

Figure 5:
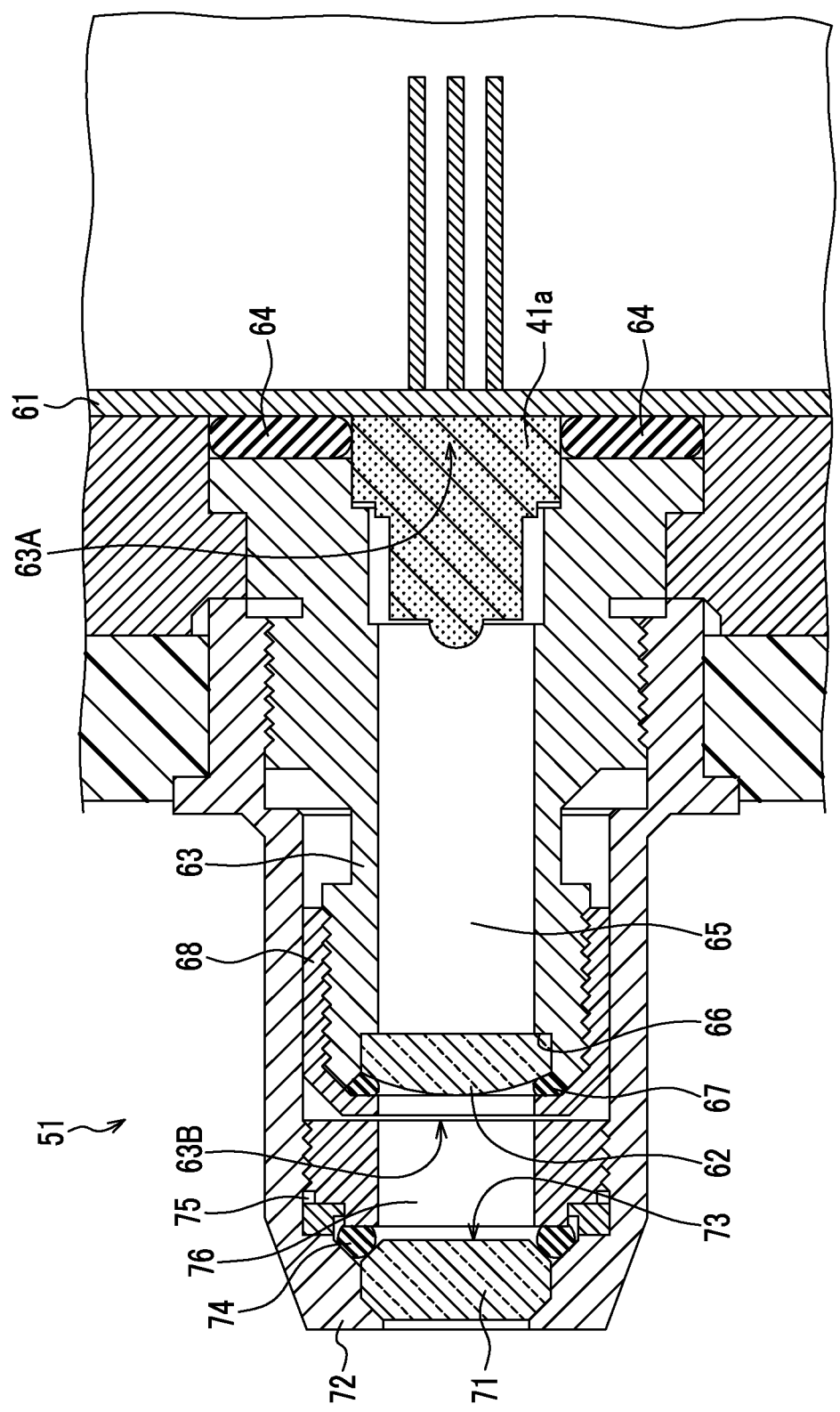
FIG. 5 is a partial sectional view taken along line V-V illustrated in FIG. 3.

A partially sectional view taken along line V-V of the light emitting connector part 51 illustrated in FIG. 3 is illustrated in FIG. 5. As illustrated in FIG. 5, the light emitting connector part 51 has the light emitting element 41a attached on a substrate 61, a lens 62, and a substantially cylindrical hollow metal member 63 having two openings 63A and 63B communicating with each other. The light emitting element 41a is press-fitted into one opening 63A of the hollow metal member 63, and a region between the light emitting element 41a, the hollow metal member 63, and the substrate 61 is filled with a sealant 64 having an adhesive property having silicon as a main component. A gap between the light emitting element 41a and the hollow metal member 63 is sealed with a sealant 64 serving as a second sealing member, and a gap between the substrate 61 and the hollow metal members 63 is sealed with this sealant.

The lens 62 is disposed in the other opening 63B of the hollow metal member 63. The lens 62 is fixed by a fixing member 68 from the opening 63B side via an O ring 67 formed of an elastic body in a state where the lens is supported by a stepped part 66 provided in a cavity part 65 of the hollow metal member 63. The O ring 67 is locked between the lens 62 and the hollow metal member 63, and the fixing member 68 is threadedly engaged with an outer peripheral surface of the hollow metal member 63, and fixes the O ring 67 between the lens 62 and the hollow metal member 63 in a state in which the O-ring is sandwiched between the fixing member and the lens 62. In the present embodiment, a first sealing member is constituted of the O ring 67 and the fixing member 68, and an O ring 67 serving as a waterproofing member that is deformed by pressing force from the fixing member 68 seals a gap between the lens 62 and the hollow metal members 63.

The opening 63B of the hollow metal member 63 where the lens 62 is disposed is located on the distal end side of the light emitting connector part 51 formed in a convex shape, and the opening 63A is located on the inner side of the light emitting connector part 51. A transparent member 71 for protecting the lens 62 is provided further toward the distal end side than the opening 63B of the hollow metal member 63 which the lens 62 is disposed in and the fixing member 68 is threadedly engaged with. The transparent member 71 is provided in a cavity on one opening 73 side of a holding member 72 that has two openings that communicate with each other, and blocks the opening 73. The transparent member 71 is fixed by a holddown member 75 that is inserted into the cavity from the other opening of the holding member 72 via an O ring 74 formed of an elastic body. An O ring 74 as a third sealing member is locked between the transparent member 71 and the holding member 72, and the holddown member 75 is threadedly engaged with an inner peripheral surface of the holding member 72, and presses the O ring 74 against the opening 73 side. The O ring 74 deformed by a pressing force from the holddown member 75 seals a gap between the transparent member 71 and the holding member 72.

The holding member 72 having the transparent member 71 fixed to the opening 73 side is fitted into the hollow metal member 63 from the other opening, and is fixed to the hollow metal member 63 by being threadedly engaged with the outer peripheral surface of the hollow metal member 63. A closed space (hollow structure) 76 is formed between the transparent member 71 and the lens 62 in a state where the holding member 72 is fixed to the hollow metal member 63. Since the gap between the transparent member 71 and the holding member 72 is sealed with the O ring 74, the space (hollow structure) 76 is hermetically sealed.

In the light emitting connector part 51 configured as described above, the light emitted from the light emitting element 41a is transmitted through the lens 62 and the transparent member 71 and is output from a distal end of the light emitting connector part 51 to the outside. In addition, the light receiving connector part 52 has the same configuration as the light emitting connector part 51 except for including the light receiving element 41b instead of the light emitting element 41a.

As described, in the present embodiment, the light emitting element 41a is press-fitted into one opening 73 side of the hollow metal member 63, and the lens 62 is provided on the other opening 73 side. Therefore, the alignment between the light emitting element 41a and the lens 62 can be reliably performed. Additionally, the gap between the light emitting element 41a and the hollow metal member 63 is sealed with the sealant 64 and the gap between the lens and the hollow metal members 63 is also sealed with the O ring 67 fixed by the fixing member 68. Therefore, the airtightness of the cavity part 65 of the hollow metal member 63 where the light emitting element 41a is present can be sufficiently maintained. Moreover, since the gap between the transparent member 71 and the holding member 72 provided closer to the distal end side of the light emitting connector part 51 than the lens 62 is sealed with the O ring 74, the space (hollow structure) 76 formed between the lens 62 and the transparent member 71 is hermetically sealed.

Therefore, even if a cleaning liquid or water is applied to the connector 13 with high pressure when cleaning work is performed in a state where the electronic endoscope 2 is detached from the processor device 3, the airtightness of the cavity part 65 of the hollow metal member 63 where the light emitting element 41a is present or the airtightness of the space (hollow structure) 76 formed between the lens 62 and the transparent member 71 is sufficiently maintained.

As described above, the endoscope apparatus disclosed in the present specification includes a connector part that is connected to an external device and transmits and receives a light signal to and from the external device. The connector part includes a hollow metal member having two openings that communicate with each other; an optical semiconductor element that is fixed to one opening side of the hollow metal member so as to be capable of sealing the periphery of the one opening; a lens that is provided on the other opening side of the hollow metal member; and a first sealing member that fixes the lens to the hollow metal member and seals a gap between the lens and the hollow metal member.

Additionally, the connector part includes a second sealing member that seals a gap between a substrate, to which the optical semiconductor element is attached, and the hollow metal member.

Additionally, the connector part includes a second sealing member that seals a gap between the optical semiconductor element and the hollow metal member.

Additionally, the first sealing member includes a waterproofing member that is locked between the lens and the hollow metal member and is formed of an elastic body; and a fixing member that is engaged with the hollow metal member and fixes the waterproofing member between the lens and the hollow metal member.

Additionally, the second sealing member includes a sealant.

The lens is provided on the distal end side of the connector part with respect to the optical semiconductor element, and a transparent member for protecting the lens is provided closer to the distal end side of the connector part than the lens.

Additionally, the endoscope apparatus further includes a holding member that holds the transparent member and forms a closed space (hollow structure) between the transparent member and the lens; and a third sealing member that hermetically seals the space (hollow structure).

Additionally, the optical semiconductor element is a light emitting element.

What is claimed is:

1. An endoscope apparatus comprising a connector part that is connected to an external device and transmits and receives a light signal to and from the external device,
wherein the connector part comprises:
a hollow metal member having a first opening and a second opening that communicate with each other, wherein the first opening is disposed at one end of the hollow metal member, and the second opening is disposed at the other end of the hollow metal member;
an optical semiconductor element that is fixed in the first opening of the hollow metal member; and
a lens that is provided in the second opening of the hollow metal member,
wherein the light signal is outputted from the optical semiconductor element to the external device through the lens, or
the light signal is inputted from the external device to the optical semiconductor element through the lens.

2. The endoscope apparatus according to claim 1, wherein the connector part is formed in a convex shape, and
the lens is located on a distal end side of the connector part formed in the convex shape.

3. The endoscope apparatus according to claim 2, wherein the connector part that is formed in the convex shape is fitted to a connector part of the external device that is formed in a concave shape.

4. The endoscope apparatus according to claim 3, wherein the connector part and the external device are insulated from each other, and transmit and receive an electric power.

5. The endoscope apparatus according to claim 4, wherein a pair of coils are respectively provided in the connector part and the external device, and the pair of the coils are arranged to face each other with non-contact, in a state where the connector part and the external device are connected to each other, and transmit electric power with mutual insulation being maintained using electromagnetic induction.

6. The endoscope apparatus according to claim 3, further comprising:
a first sealing member that fixes the lens to the hollow metal member and seals a gap between the lens and the hollow metal member.

7. The endoscope apparatus according to claim 2, wherein the connector part and the external device are insulated from each other, and transmit and receive an electric power.

8. The endoscope apparatus according to claim 7, wherein a pair of coils are respectively provided in the connector part and the external device, and the pair of the coils are arranged to face each other with non-contact, in a state where the connector part and the external device are connected to each other, and transmit electric power with mutual insulation being maintained using electromagnetic induction.

9. The endoscope apparatus according to claim 7, further comprising:
a first sealing member that fixes the lens to the hollow metal member and seals a gap between the lens and the hollow metal member.

10. The endoscope apparatus according to claim 2, further comprising:
a first sealing member that fixes the lens to the hollow metal member and seals a gap between the lens and the hollow metal member.

11. The endoscope apparatus according to claim 1, wherein the connector part and the external device are insulated from each other, and transmit and receive an electric power.

12. The endoscope apparatus according to claim 11, wherein a pair of coils are respectively provided in the connector part and the external device, and the pair of the coils are arranged to face each other with non-contact, in a state where the connector part and the external device are connected to each other, and transmit electric power with mutual insulation being maintained using electromagnetic induction.

13. The endoscope apparatus according to claim 11, further comprising:
a first sealing member that fixes the lens to the hollow metal member and seals a gap between the lens and the hollow metal member.

14. The endoscope apparatus according to claim 1, further comprising:
a first sealing member that fixes the lens to the hollow metal member and seals a gap between the lens and the hollow metal member.

15. The endoscope apparatus according to claim 14, wherein the connector part comprises a second sealing member that seals a gap between a substrate, to which the optical semiconductor element is attached, and the hollow metal member.

16. The endoscope apparatus according to claim 15, wherein the second sealing member includes a sealant.

17. The endoscope apparatus according to claim 14, wherein the connector part comprises a second sealing member that seals a gap between the optical semiconductor element and the hollow metal member.

18. The endoscope apparatus according to claim 14, wherein the first sealing member has:
a waterproofing member that is locked between the lens and the hollow metal member and is formed of an elastic body; and
a fixing member that is engaged with the hollow metal member and fixes the waterproofing member between the lens and the hollow metal member.

19. The endoscope apparatus according to claim 1, wherein the lens is provided on a distal end side of the connector part with respect to the optical semiconductor element, and
wherein a transparent member for protecting the lens is provided closer to the distal end side of the connector part than the lens.

20. The endoscope apparatus according to claim 19, further comprising:
a holding member that holds the transparent member and forms a closed hollow structure between the transparent member and the lens; and
a third sealing member that hermetically seals the hollow structure.

* * * * *